United States Patent [19]

Breddin et al.

[11] 4,066,360

[45] Jan. 3, 1978

[54] DEVICE FOR MEASURING AND RECORDING SPONTANEOUS BLOOD PLATELET AGGREGATION IN PLATELET-RICH CITRATED PLASMA

[75] Inventors: Klaus Breddin, Walldorf; Wolfgang Schremmer, Obermelsungen, both of Germany

[73] Assignee: B. Braun Melsungen Aktiengesellschaft, Melsungen, Germany

[21] Appl. No.: 550,920

[22] Filed: Feb. 19, 1975

[30] Foreign Application Priority Data

Feb. 21, 1974 Germany .............................. 2408214

[51] Int. Cl.² .......................... G01N 33/16; B01L 9/06
[52] U.S. Cl. ........................................ 356/39; 356/246
[58] Field of Search .................................. 356/39–42, 356/197, 208, 246; 23/230 B; 73/64.1; 128/28 G

[56] References Cited

U.S. PATENT DOCUMENTS

| | | | |
|---|---|---|---|
| 3,302,452 | 2/1967 | Leslie | 73/64.1 |
| 3,582,218 | 6/1971 | Anderson | 356/246 |
| 3,679,315 | 7/1972 | Laucournet | 356/246 |
| 3,754,866 | 8/1973 | Ritchie et al. | 356/39 |
| 3,777,172 | 12/1973 | Clarke | 356/39 |
| 3,876,379 | 4/1975 | Ghim | 23/230 B |

OTHER PUBLICATIONS

Frojmovic, M. M., "Quantitative Parameterization of the Light Transmission Properties of Citrated, Platelet-Rich Plasma as a Function of Platelet and Adenosine Diphosphate Concentrations and Temperature," Jr. Lab. and Clin. Med., July, 1973, pp. 137–153.

Haslam, R. V. "Role of Adenosine Diphosphate in Aggregation of Human Blood-Platelets by Thrombin and by Fatty Acids," Nature, May, 1964, pp. 765–768.

Frojmovic et al., "Blood Cell Structure-Function Studies; Light Transmission and Attenuation Coefficients of Suspensions of Blood Cells and Model Particles at Rest and with Stirring," Jr. Lab & Clin. Med. Aug. 1975, pp. 326–342.

Born, G. V. R., "Aggregation of Blood Platelets by Adenosine Diphosphate and its Reversal," Nature June 9, 1962, pp. 927–929.

Schmid-Schönbein et al., "A Counter-Rotating Rhedscope Chamber for the Study of the Microrheology of Blood Cell Aggregation by Microscopic Observation and Microphotometry" Microvascular Research, 6, 366–376, (1973).

*Primary Examiner*—John K. Corbin
*Assistant Examiner*—Wm. H. Punter
*Attorney, Agent, or Firm*—Curtis, Morris & Safford

[57] ABSTRACT

A device for measuring and recording spontaneous blood platelet aggregation in platelet-rich citrated blood plasma comprising a photometer having a source of light, a photo cell, a light filter and a rotating disk cuvette for receiving the platelet-rich citrated plasma to be tested.

12 Claims, 5 Drawing Figures

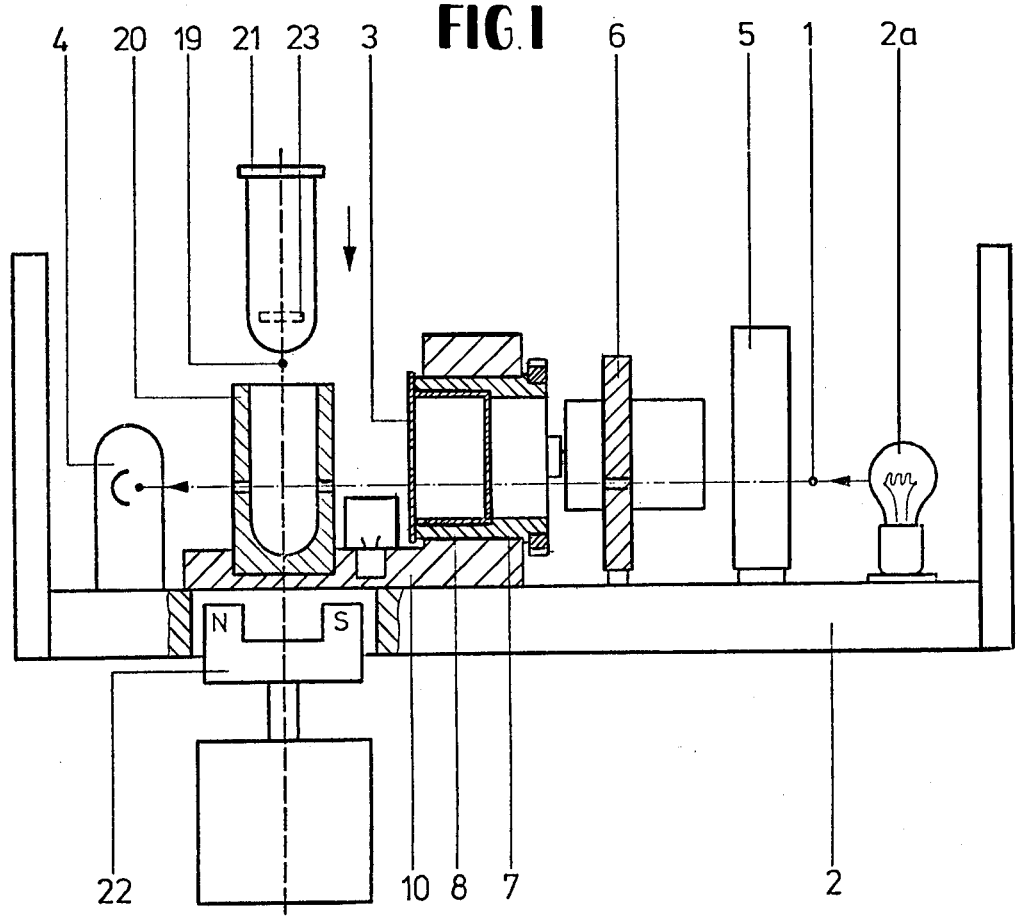
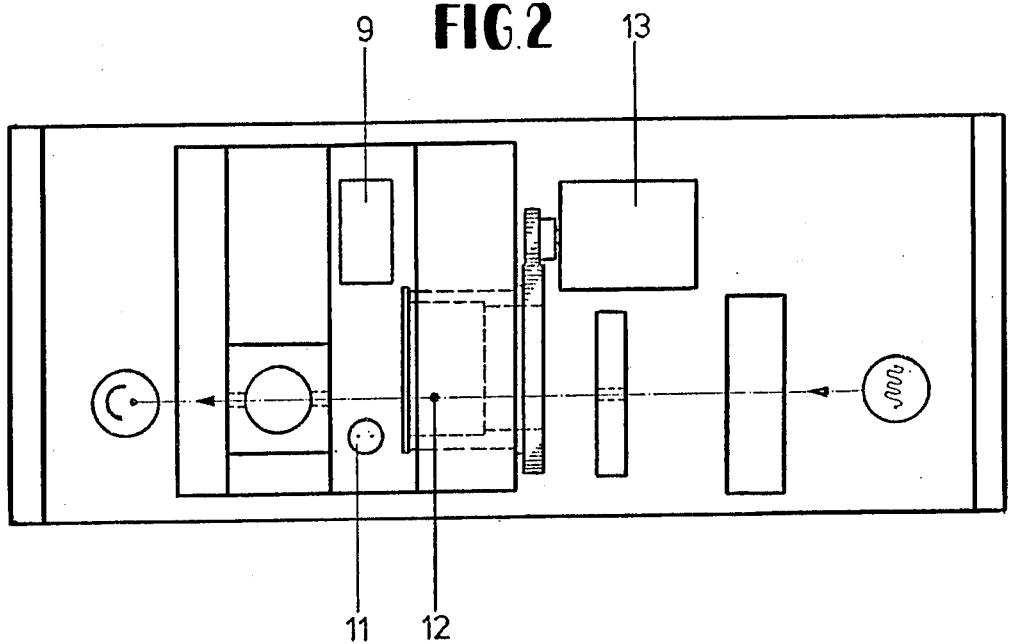

FIG.3
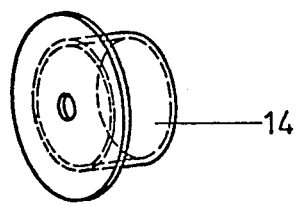
FIG.4
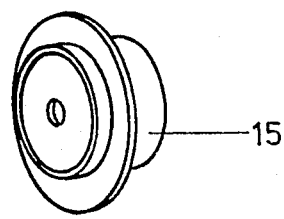
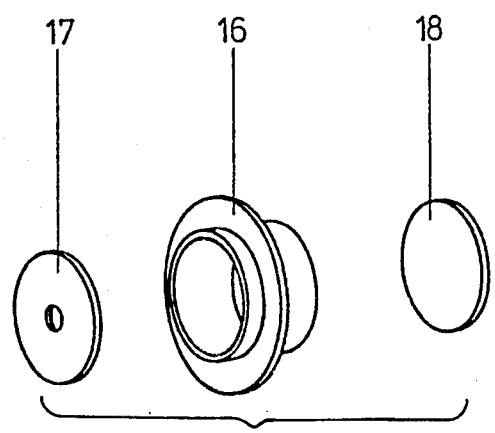
FIG. 5

DEVICE FOR MEASURING AND RECORDING SPONTANEOUS BLOOD PLATELET AGGREGATION IN PLATELET-RICH CITRATED PLASMA

The present invention relates to a device for the photometric measuring and recording of the spontaneous aggregation of blood platelets (thrombocytes) in platelet-rich citrated plasma.

The adhesiveness of the thrombocytes to the vessel-wall and the formation of platelet aggregates are two important physiological processes in the staunching or clotting of blood after injuries and probably in the continuous sealing of blood vessel walls as well.

Furthermore, the adhesiveness of thrombocytes to changed vessel wall areas and the subsequent platelet aggregation represent the first stages in the formation of arterial and venous thromboses.

Investigations into the thrombocyte aggregation are of great importance for the clinician with regard to the detection of certain blood diseases based on a reduced function of the thrombocytes, as well as with regard to the determination of an increased tendency to aggregation of the blood platelets.

An increased tendency to aggregation can be found with patients suffering from diabetes mellitus and progressive arteriosclerosis, as well as after a cardiac infarct, but also in the case of venous thromboses. It can be shown that the increased platelet aggregation is an important risk factor for thromboembolic complications in the case of arteriosclerosis and probably also for the progression of arteriosclerosis itself.

For some years, drugs have been available which inhibit the aggregation of thrombocytes and may therefore be used for the prophylaxis of thrombosis. The effect of these drugs may be controlled reliably by means of the new device.

Several methods are known for the determination of blood platelet aggregation:

With the aid of the so-called retention tests the number of thrombocytes before and after the passage of blood or blood plasma through a filter, e.g., of glass beads or polyamide fibres, is determined. The retention is defined as percentage of the blood platelets retained in the filter. This method is inaccurate because of the very wide range. Moreover, the adhesiveness of the blood platelets differs depending on the filter material used.

The result depends on the adhesiveness as well as on the aggregation of the platelets.

Literature

Moolten, S. E., L. Vroman: The adhesiveness of blood platelets in thromboembolism and hemorrhagic disorders. I. Measurement of platelet adhesiveness by glasswool filter. Amer. J. clin. Path. 19: 701 (1949)

Hellem, A. J.: The adhesiveness of human blood platelets in vitro. Scand. J. clin. Lab. Invest. Suppl. 51: 1 (1960)

Salzmann, E. W.: Measurement of platelet adhesiveness. J. Lab. clin. Med. 62: 724 (1963)

Morris, C. D. W.: Acetylsalicyclic acid and platelet stickiness. Lancet 1967/I,279

In another method the change of the optical density of a platelet-rich blood plasma is measured after the addition of so-called inducers. According to this photometric method, platelet-rich plasma in a small vertical glass tube, which is placed in the path of rays of a photometer, is vigorously stirred by means of a small magnet. The aggregation is induced by the addition of adenosine diphosphate, collagen or adrenaline and the change of the optical density is recorded.

Literature

Born, G. V. R.: Quantitative investigations into the aggregation of blood platelets, J. Physiol. 162: 67 (1962)

O'Brien, J. R.: The adhesiveness of native platelets and its prevention. J. clin. Path. 14: 140 (1961)

This method allows the specific determination of the aggregation. Furthermore, the effect of drugs inhibiting the aggregation may be judged from the aggregation induced by collagen, etc. However, by means of this method it is not possible to prove a spontaneously increased tendency to aggregation of the blood platelets. The method is not suitable for detecting a tendency to thrombosis.

In a modification of this method plasma circulates in a circulation system and the thrombocyte aggregates are removed by means of a filter. The determination is carried out in a through-run cuvette. The aggregation is induced by collagen. This method is likewise unsuitable for determining the spontaneously increased aggregation.

Literature

Heinrich, D. and L. Roka: Methode zur Bestimmung der Thrombozyten-Aggregation. KLIN.-WSCR 48: 235 (1969)

Breddin developed a method to prove, in particular, the spontaneous tendency to aggregation of the plasma. Platelet-rich citrated plasma is rotated at 37° C in siliconized glass flasks having a capacity of 20 ml. The thrombocytes may then come into contact with one another. The rotated and diluted plasma is used to coat plastic slides. After a contact time of 30 to 45 minutes, the preparations are fixed, oxidized, stained and examined microscopically. This method allows the reliable and reproducible determination of a spontaneously increased aggregation of the thrombocytes. Also the effect of aggregation inhibitors may be tested in vitro and in vivo if there is an increased aggregation. However, the course of aggregation cannot be recorded continuously by this method. The microscopic examination may lead to subjective errors. In the case of the maximal aggregation it is not possible to determine the period of time after which the state of aggregation has been reached. As a result, an important possibility of differentiation for clinical examinations is missing. Moreover, the test result is available after 90 minutes at the earliest. Furthermore, the quantity of plasma required is relatively large.

Literature

Breddin, K.: Die Thrombozytenfunktion bei haemorrhagischen Diathesen, Thrombosen und Gefaesskrankheiten. Thrombos. Dlathes. haemorrh. Suppl. 27 (1968)

Breddin, K., J. Bauke: Thrombozytenagglutination und Gefaesskrankheiten. Blut 11: 144 (1965)

It is the object of the invention to provide a device of simple construction which is easy to handle and always ready for use and which allows one to continuously measure and record in a reliable manner the spontaneously increased tendency to aggregation in blood platelet-rich citrated plasma and moreover to measure the increased tendency to aggregation with patients suffering from blood-vessel diseases and which device may be used for serial examinations of healthy persons and those suffering from blood-vessel diseases. For each test the quantity of blood required should amount to about 2 ml to about 5 ml of citrated blood, i.e. to about 0.5 to about 1 ml or less of citrated plasma.

Further object of the invention is to use said device for determining the effect of aggregation-inhibiting drugs in vitro by the addition of the inhibiting substance to the platelet-rich plasma, as well as in vivo.

Since normal plasma can be modified by the addition of various heparinoides in such a way that it has a maximal platelet-aggregating effect, it is also the object of the invention to measure by means of the same measuring device the aggregation-inhibiting effect of drugs.

These objects were achieved in accordance with the invention by means of the new measuring and recording device.

The invention is illustrated by means of the drawings in which

FIG. 1 is a longitudinal section of an embodiment of the measuring and recording device according to the invention;

FIG. 2 is a top plan view of the device shown in FIG. 1;

FIG. 3 is a diagrammatic representation of a cuvette for single use in the device of FIG. 1;

FIG. 4 is a diagrammatic representation of a multi-cuvette; and

FIG. 5 is an exploded perspective view of the component parts of the cuvette of FIG. 4.

The component parts of the device and their interaction for measuring and recording the spontaneous aggregation of the blood platelets will be described with reference to the diagrammatic representations in FIGS. 1 and 2.

In the path of rays 1 of a photometer 2 a heatable disk cuvette 3 is rotating. The platelet-rich blood plasma is filled into this disk cuvette. When a platelet aggregation takes place in this plasma, its light transmittance increases and the optical density decreases. This transmission is measured and recorded as a curve by means of a commercial potentiometric recorder.

The measurement is effected by means of a photometer 2 having a source of light 2a, using a light filter 5 of about 500 to 650 nm, preferably 546 nm.

Between light filter 5 and disk cuvette 3 there is a diaphragm 6, with a diameter of the aperture of about 0.5 to 3 mm, preferably 2 mm, for limiting the light ray.

The disk cuvette 3 is placed in a rotational drum 7 where it is secured by means of a holding device, for example an O-ring 8. The rotational drum 7 is incorporated in a metal block 10, e.g., of aluminum, which may be heated by a resistance unit 9. Tempering of the disk cuvette 3 is thus effected according to the principle of the block thermostat: A resistance unit 9 heats the aluminum block 10 and the latter transfers the heat to the disk cuvette 3. The stabilization of the temperature, for example at 37° ± 0.5° C, is effected over a suitable automatic control system, for example an NTC-resistor serving as thermometer probe 11. The temperature stability is reached after about 15 to 20 minutes.

The disk cuvette 3 rotates at a speed of about 10 to about 60 revolutions per minute, advantageously of about 20 revolutions per minute. It is inserted into the path of rays of the photometer in such a manner that the light ray passes through its right lower quadrant 12. The measuring place is situated about 5 mm below the horizontal diameter of the disk and about 4 mm on the right of the vertical diameter of the disk. A speed-stabilized motor 13 serves as drive.

Two types of cuvettes may be used, i.e., a cuvette 14 for single use consisting, for example, of glass or a transparent plastic material, for example polymethylmethacrylate or polystyrene, or a multi-cuvette 15 consisting of the same material and which may be used several times. The multi-cuvette comprises a drum 16, for example of polyvinyl chloride, and two cover disks 17 and 18, for example of polymethylmethacrylate. The cuvettes have an outer diameter of about 20 mm and an inner diameter of about 18 mm.

For practice, it is suitable to use the new device for recording the spontaneous aggregation of blood platelets also for the known photometric method for measuring the induced aggregation, all in one device. Although it is possible to induce an aggregation in every normal plasma also in the disk cuvette by the addition of adenosine diphosphate, collagen, thrombin or adrenalin, it is not possible in this case to ascertain whether the aggregation has occurred under the influence of the inducer or "spontaneously" under the influence of plasma proteins.

For the detection of special thrombocyte defects (thromboasthenia, thrombopathy) as well as for the examination of thrombocyte aggregation inhibitors it is therefore advantageous to use the new device also for measuring the induced aggregation—(Method according to G. V. R. Born: Quantitative investigations into the aggregation of blood platelets, J. Physiol. 162: 67 (1962).

As a result, two different biological reactions may be determined, the special advantage of the new device residing in the fact that the activity in the plasma inducing the spontaneous aggregation is made visible.

For measuring the inductive aggregation, a heatable measuring tube 21 instead of a heatable disk cuvette is inserted into the path of rays of the photometer 2, said measuring tube being suitably arranged in a metal block 20 in a receiving bore. Below the holding means for the metal block there is a rotary magnet 22 driven by a speed-stabilized motor. The magnet speed is 500 to 1000 revolutions per minute, preferably 800 revolutions per minute.

The blood plasma is mixed by a stirring magnet 23 placed in the measuring tube and coated with polytetrafluoroethylene and having a diameter of about 2 mm and a length of about 5 mm. In this arrangement the path of light rays passes through the diaphragm, the empty rotational drum and then through the measuring tube of the photo cell. Siliconized small glass or plastic tubes having an inner diameter of about 9 to 11 mm are used as measuring tubes.

The blood platelet-rich citrated plasma for carrying out the photometric measuring and recording of the spontaneous aggregation of the blood platelets according to the invention may be obtained from citrated blood by short centrifugation (about 1 to 1.5 minutes at 100 to 150 G). The blood is withdrawn and the citrated blood is obtained in such a manner that 10 ml of freshly withdrawn venous blood is thoroughly mixed with 1 ml of a 3.8% aqueous sodium citrate solution.

For each test, about 0.5 to about 1 ml of citrated plasma, corresponding to about 2 to about 5 ml of citrated blood, is used.

We claim:

1. A device for the photometric measuring of the spontaneous aggregation of blood platelets in blood platelet rich citrated plasma, comprising a photometer including a light source and a photo cell aligned with the light source to receive light rays therefrom, a light filter positioned between the light source and photo cell, a diaphragm having an aperture formed therein in a predetermined position and located between said filter and photo cell whereby the aperture in the diaphragm passes a well defined column of light rays from the light source to the photo cell; a hollow disc cuvette rotatably mounted in the photometer between said diaphragm and photocell for rotation in a vertical plane with its central axis in a horizontal plane, said vertical plane being located in and transverse to the path of light rays passing through the diaphragm, said cuvette containing a supply of citrated plasma to be measured; means for heating said disc cuvette to a predetermined temperature; and means for rotating said disc cuvette at a speed of between 10 and 60 revolutions per minute; said disc cuvette being located in the photometer at a position with respect to said diaphragm wherein the light rays from the diaphragm pass through a lower quadrant of the disc cuvette with the disc viewed facing the diaphragm.

2. A device as defined in claim 1 wherein said means for rotating the disc cuvette rotates the disc cuvette at a speed of 20 rpm.

3. A device for the photometric measuring of the spontaneous aggregation of blood platelets in blood platelet rich citrated plasma, comprising a photometer including a light source and a photo cell aligned with the light source to receive light rays therefrom, a light filter positioned between the light source and photo cell, a diaphragm having an aperture formed therein in a predetermined position and located between said filter and photo cell whereby the aperture in the diaphragm passes a well defined column of light rays from the light source to the photo cell; a hollow disc cuvette rotatably mounted in the photometer between said diaphragm and photocell for rotation in a vertical plane with its central axis in a horizontal plane, said vertical plane being located in and transverse to the path of light rays passing through the diaphragm, said cuvette containing a supply of citrated plasma to be measured; means for heating said disc cuvette to a predetermined temperature; and means for rotating said disc cuvette at a speed of between 10 and 60 revolutions per minute; said disc cuvette being located in the photometer at a position with respect to said diaphragm wherein the light rays from the diaphragm pass through the lower right quadrant of the disc cuvette with the disc viewed facing the diaphragm.

4. A device as defined in claim 3 wherein said heating means maintains said disc cuvette at a constant temperature of 37° ± 0.5° C.

5. A device as defined in claim 4 wherein said means for rotating the disc cuvette rotates the disc cuvette at a speed of 20 rpm.

6. A device as defined in claim 5 wherein said disc cuvette comprises a hollow drum open at opposite ends, and a pair of removable covers discs removably secured to the ends of the drum.

7. A device as defined in claim 6 wherein the cuvette has an outer diameter of approximately 20 mm and an inner diameter of about 18 mm.

8. The method of measuring the spontaneous aggregation of blood platelets in blood platelet rich citrated plasma comprising the steps of placing a supply of blood platelet rich citrated plasma in a hollow transparent disc cuvette; placing said disc in a vertical plane with its central axis in a horizontal plane; heating said cuvette to a predetermined relatively stable temperature, rotating the disc cuvette containing said citrated plasma in said vertical plane about its central axis at a speed of rotation of between 10 and 60 revolutions per minute and passing a light beam transversely through said disc from a light source to a photocell along a horizontal path which is generally perpendicular to the plane in which said disc rotates; and producing a well defined beam of light from the light source and positioning the disc cuvette between the light source and photocell such that said beam of light passes through a lower quadrant of the disc cuvette with the disc viewed facing the diaphragm.

9. The method of measuring the spontaneous aggregation of blood platelets in blood platelet rich citrated plasma comprising the steps of placing a supply of blood platelet rich citrated plasma in a hollow transparent disc cuvette; placing said disc in a vertical plane with its central axis in a horizontal plane; heating said cuvette to a predetermined relatively stable temperature, rotating the disc cuvette containing said citrated plasma in said vertical plane about its central axis at a speed of rotation of between 10 and 60 revolutions per minute and passing a light beam transversely through said disc from a light source to a photocell along a horizontal path which is generally perpendicular to the plane in which said disc rotates; and including the step of producing a well defined beam of light from the light source and positioning the disc cuvette between the light source and photocell such that said beam of light passes through the lower right quadrant of the disc cuvette with the disc viewed facing the diaphragm.

10. The method as defined in claim 9 wherein said rotating step comprises the step of rotating the disc cuvette at a rotary speed of 20 rpm.

11. The method as defined in claim 10 wherein said heating step comprises the step of maintaining said disc cuvette at a constant temperature of 37° ± 0.5° C.

12. The method as defined in claim 11 wherein the step of placing said supply of citrated plasma in the disc cuvette comprises the step of placing between 0.5 and 1 ml of citrated plasma therein.

* * * * *